United States Patent
Heller et al.

(10) Patent No.: US 6,846,398 B1
(45) Date of Patent: Jan. 25, 2005

(54) DEVICE AND METHOD FOR MINIATURIZED, HIGHLY PARALLEL ELECTROPHORETIC SEPARATION

(75) Inventors: Christoph Heller, Berlin (DE); Holger Eickhoff, Berlin (DE); Sven Behr, Berlin (DE)

(73) Assignee: Max-Planck-Gesellschaft zur Forderung der Wissenshaften E.V., Munich (DE)

( * ) Notice: Subject to any disclaimer, the term of this patent is extended or adjusted under 35 U.S.C. 154(b) by 0 days.

(21) Appl. No.: 09/701,908

(22) PCT Filed: Jun. 2, 1999

(86) PCT No.: PCT/EP99/03834

§ 371 (c)(1),
(2), (4) Date: Jan. 22, 2001

(87) PCT Pub. No.: WO99/64850

PCT Pub. Date: Dec. 10, 1999

(30) Foreign Application Priority Data

Jun. 10, 1998 (DE) .......................... 198 26 020

(51) Int. Cl.[7] ............................................ G01N 27/453
(52) U.S. Cl. ........................ 204/453; 204/450; 204/600; 204/604
(58) Field of Search ................................ 204/450, 453, 204/600, 604

(56) References Cited

U.S. PATENT DOCUMENTS

| | | | |
|---|---|---|---|
| 5,192,412 A | | 3/1993 | Kambara et al. |
| 5,958,203 A | * | 9/1999 | Parce et al. ................. 204/451 |
| 6,013,165 A | * | 1/2000 | Wiktorowicz et al. ...... 204/456 |
| 6,086,825 A | * | 7/2000 | Sundberg et al. ........... 422/100 |
| 6,406,604 B1 | * | 6/2002 | Guzman ..................... 204/601 |
| 6,447,727 B1 | * | 9/2002 | Parce et al. ................. 422/100 |

FOREIGN PATENT DOCUMENTS

| | | |
|---|---|---|
| DE | 4139211 | 6/1992 |
| WO | WO 9734138 | 9/1997 |
| WO | WO 9804909 | 2/1998 |

OTHER PUBLICATIONS

Carlo S. Effenhauser et al, "*Integrated Chip–Based Capillary Electrophoresis*", "Electrophoresis" 1997, Germany, vol. 18, pp. 2203–2213.

Christine Evans "*Direct On–Line Injection in Capillary Electrophoresis*", "Analytical Chemistry " Aug. 1, 1997, U.S.A., vol. 69, pp. 2952–2954.

Woolley et al, "*Ultra–High–Speed DNA Sequencing Using Capillary Electrophoresis Chips*", "Analytical Chemistry" Oct. 15, 1995, U.S.A., vol. 67, pp. 3676–3680.

Woolley et al. "*High–Speed DNA Genotyping Using Microfabricated Capillary Array Electrophoresis Chips*", "Analytical Chemistry" Jun. 1, 1997, U.S.A., vol. 69, pp. 2181–2186.

* cited by examiner

Primary Examiner—Kaj K. Olsen
(74) Attorney, Agent, or Firm—Ryndak & Suri; Vangelis Economou

(57) ABSTRACT

In an electrophoresis device with numerous separation channels S loadable with samples, samples are loaded by applying samples in a shared injection channel I intersecting the separation channels S near a point where the injection channel I crosses one of the separation channels S. During exposure to a voltage in the injection channel, the samples are transferred to the separation channels S, and there electrophoretically separated.

9 Claims, 2 Drawing Sheets

DEVICE AND METHOD FOR MINIATURIZED, HIGHLY PARALLEL ELECTROPHORETIC SEPARATION

The invention relates to an electrophoresis device with a plurality of separation channels that can be separately loaded with samples, in particular to an electrophoresis device manufactured as a micro system in chip form, and an electrophoresis procedure involving the use of such a device.

The electrophoretic separation of substances and substance mixtures is an analytical procedure that is particularly widespread in biochemistry and molecular biology. The substances to be separated are separated during exposure to an electric field and specifically detected in a separating medium. In particular for analyzing complex genomes and proteomes, it is necessary to analyze a very high number of different samples (scale roughly $10^5$ to $10^7$). This is the reason for the interest in analysis systems whose operation is as automated as possible and which have a high sample throughput.

The separation rate, sensitivity and potential for automation has been improved or simplified relative to the conventional electrophoresis procedure by capillary electrophoresis, which has been generally known for roughly 10 years. In capillary electrophoresis, the separating medium is in a capillary, which leads from a sample reservoir to a collector. Even though the use of capillaries offers the advantage of a relatively simple adjustment of the capillary device relative to certain sample reservoirs, further development using micro system technology has resulted in the miniaturization of capillary electrophoresis generally known for roughly the last 5 years.

In miniaturized capillary electrophoresis, the separating medium is located in micro-channels, which are processed as structures in solid-state carrier materials, e.g., silicon or plastics. These electrophoresis devices in chip form offer the advantages of a high separation rate, a lower voltage required for achieving comparable separating field strengths, and a more cost-effective large-scale manufacture as a disposable product, but also present disadvantages when loading or injecting samples in the separation channels. Specifically, injection must take place as precisely and reproducibly as possible relative to the injection site and injection volume.

Figure 3:
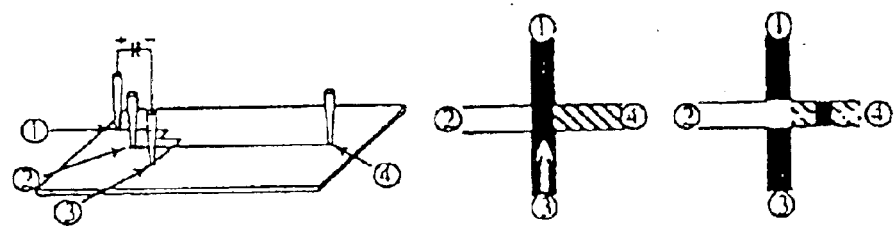

Known from publications by A. T. Woolley et al. in "Anal. Chem.", Vol. 67, 1995, p. 3676, and in "Anal. Chem.", 1997, Vol. 69, p. 2181, are electrophoresis chips with channel structures, which will be described below drawing reference to FIGS. 3 and 4. The basic structure of conventional, miniaturized electrophoresis devices consists of interlaced channels for injection or separation. In FIG. 3, an injection channel is provided between reservoirs 1 and 3, and a separation channel is provided between reservoirs 2 and 4. During separation, a corresponding electrode arrangement first subjects the injection channel to a voltage for transporting the sample (blackened) to be separated into the interlaced area. Separation then takes place in the separation channel (dashed). The mentioned intersecting structure has the following disadvantages.

The reservoirs and electrode arrangements take up a lot of space, which limits the number of electrophoresis separation channels on the chip. Due to the unfavorable geometry, the channels are spaced relatively far apart, which is disadvantageous for detection. For example, if a fluorescence detection of the separated substances takes place, unfavorable imaging dimensions must be selected, or scanners must be used to scan large areas. While this can be countered by providing bent channels, this results in additional disadvantages with respect to manufacture and separation power. The level of parallelism (number of simultaneously running separation processes) is limited.

Another disadvantages lies in the high number of reservoirs and electrode arrangements. For n channels, 4n reservoirs and electrodes are required. This is associated with a high space requirement, and also with a high circuitry outlay owing to the separate actuation. The combined use of anodes and cathodes has made it possible to achieve a maximal reduction to 2n+2 electrodes thus far. Conventional chip design according to FIG. 4 (A. T. Woolley et al. in "Anal. Chem." 1997, Vol. 69, p. 2181) also allows only a slightly improved space utilization. The separation channels are diversified, and crossed at each end by a separate sample channel P. This arrangement is limited to roughly 12 channels on a 50×75 mm chip.

One basic disadvantage to conventional, miniaturized electrophoresis devices is that the sample application is generally associated with excessive sample consumption due to the absence of an adjusted interface between the micro-channels and macroscopic world. As a result, the sample reservoirs must be filled with relatively large volumes, as described, for example, by S. C. Effenhauser et al. in "Electrophoresis", 1997, Vol. 18, p. 2203. Since only about 1% of the sample reservoir volume is injected into the respective separation channel, unacceptable sample consumption results.

Due to the above disadvantages, the use of miniaturized electrophoresis devices has only been possible on a limited scale thus far.

A capillary electrophoresis system with a sample transfer from a sample capillary to a separation capillary under the influence of an electrical field is described by C. E. Evans in "Anal. Chem.", Vol. 69, 1997, p. 2952. In DE-OS 41 39 211, an electrophoresis device with a plurality of separation channels is described. The separation channels are loaded via separate channel openings. The channel openings are surrounded by a channel-shaped reservoir which is filled with a buffer after loading of the channels.

The object of the invention is to provide an improved electrophoresis device in which an increased number of separation channels can be accommodated on a chip. In particular, the improved electrophoresis device is to have an improved geometry and improved separation and detection properties. The object of the invention is also to indicate a procedure for using such an electrophoresis device, which in particular simplifies the sample application into the electrophoresis device and lowers sample consumption.

This object achieved by an electrophoresis device having an injection channel with plural exposed application areas, one are adjacent to each separation channel on a predetermined side of the respective crossing point, each application area being designed and configured for taking samples by means of a micro-dispenser and a separation method for performing electrophoresis, wherein the sample channels are loaded with samples by means of a micro-dispenser, and the samples are introduced into the injection channel near the crossing point between the injection channel and one respective separation channel for purposes of sample separation, and transferred into the separation channel by exposing the injection to an electrical field, with electrophoretic separation taking place in this separation channel.

In particular, the object of the invention is achieved by a new channel geometry, in which the transverse or sample channels of each separation channel known from the conventional crossing structures are combined into a shared injection channel, which crosses each separation channel. The injection channel is provided with an electrode arrangement that exhibits only two electrodes at its ends. The injection channel has an application area where sample loading takes place in direct proximity to each crossing point between the injection channel and the separation channel. The injection channel can also have a sample barrier on the side lying opposite the application area for each crossing point where the injection and separation channel are interlinked, so as to avoid a contamination of the next application area of the adjacent separation channel.

In a special aspect of the invention, the separation channels run continuously from one to the other end of the carrier chip. This makes it possible to use the carrier chip in a reusable electrophoresis chamber with buffer reservoirs and an electrode arrangement for generating the separating field strength. The separation channels are open at the chip ends, so that simply incorporating the carrier chips in the electrophoresis chamber can establish contact with the buffer reservoirs.

Another, particularly important aspect of the invention lies in the combination of an electrophoresis device with a sample-loading device in the form of a micro-dispenser. This micro-dispenser consists of one or more elements (pipettes, capillaries, metal pins) that can either actively or passively collect and dispense liquids. The micro-dispenser can be used to introduce smallest sample volumes (e.g., 100 pl) in a predetermined manner into specific application areas of the injection channel. For electrically charged molecules (ions), the micro-dispenser can consist of thin steel pins, which can be electrically charged. By correspondingly applying and then commutating an electrical field, the molecules can be collected and again released. Therefore, in a separation procedure according to the invention, the samples are loaded by means of a micro-dispenser that has at least one element (dispensing pipette, capillary or steel pin).

After application, the molecules (ions) can additionally be concentrated ("focused") at the beginning of the separation channel after applied in special, electrically chargeable zones ("electrodes"). After application into the application zone, an electrical field is applied at the preferably narrowest zones (e.g., 50 $\mu$m). The molecules migrate to this area, and are there retained, resulting in a concentration of the sample. Actual separation takes place thereafter.

The following advantages are achieved with the invention. The new channel geometry makes it possible to arrange the separation channels more densely. For example, roughly 10 times as many separation channels per chip surface can be accommodated than in conventional electrophoresis devices. This increases the level of parallelism of the analysis considerably. In addition, detection is simplified, and improved based on the small dimensions and more favorable object-to-image ratios. All separation channels can be designed straight. This simplifies the manufacture of the electrophoresis device and improves the separation characteristics, since the migration characteristics of the sample can be controlled better in straight channels. The number of required electrodes is reduced to four electrodes (two electrodes each for the injection channel and separation channels). This reduction is independent of the number of separation channels. This yields a considerable space savings, and simplifies the control circuitry.

The manufacture of the microstructures is simplified considerably, since separate transverse channels need not be processed. The remaining incorporation of two electrodes for the injection channel diminishes the problem of connecting metal electrode materials and chip plastics, thus reducing the costs of chip manufacture.

Loading the samples according to the invention makes it possible to reduce the sample quantity. In an electrophoresis device according to the invention, only 10 to 30% of the sample volume needs to be injected by comparison to conventional devices.

Figures 1, 2:
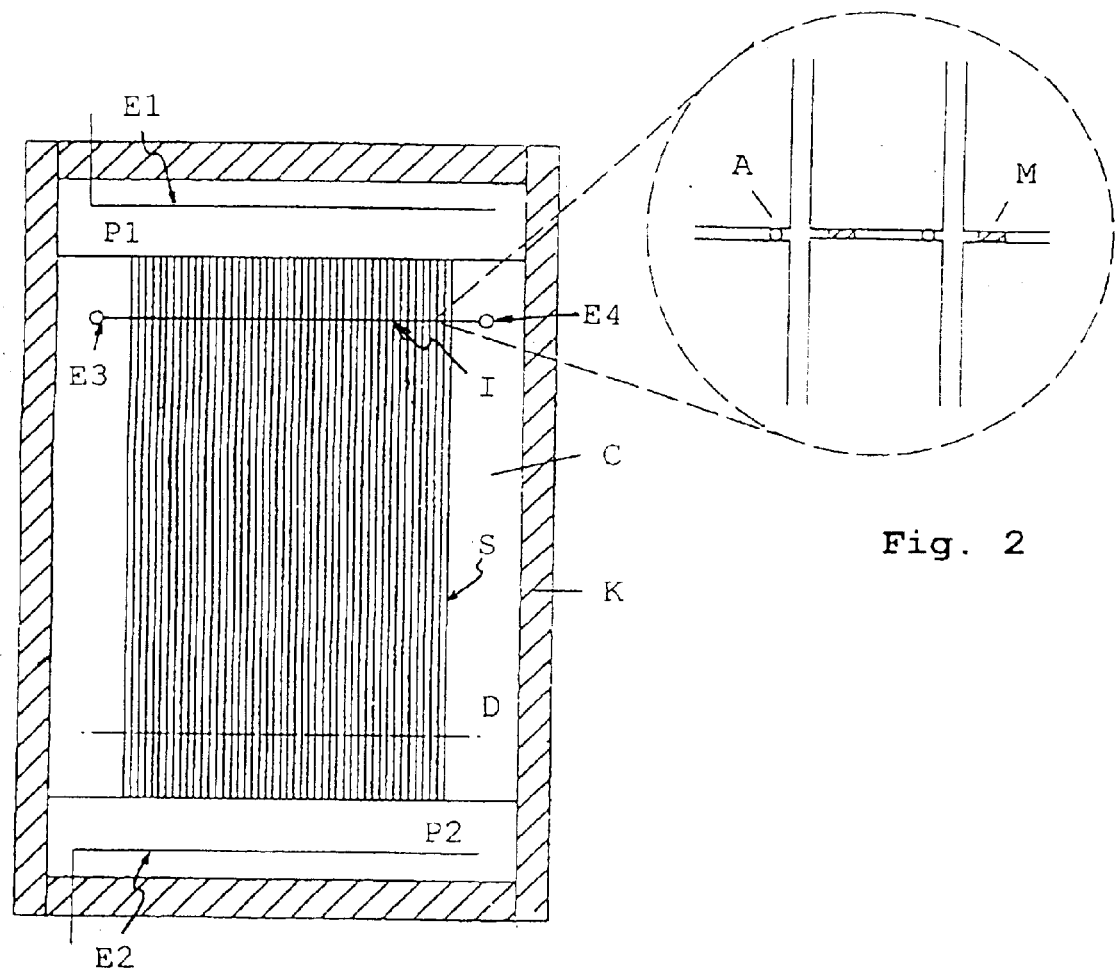
Figure 4:
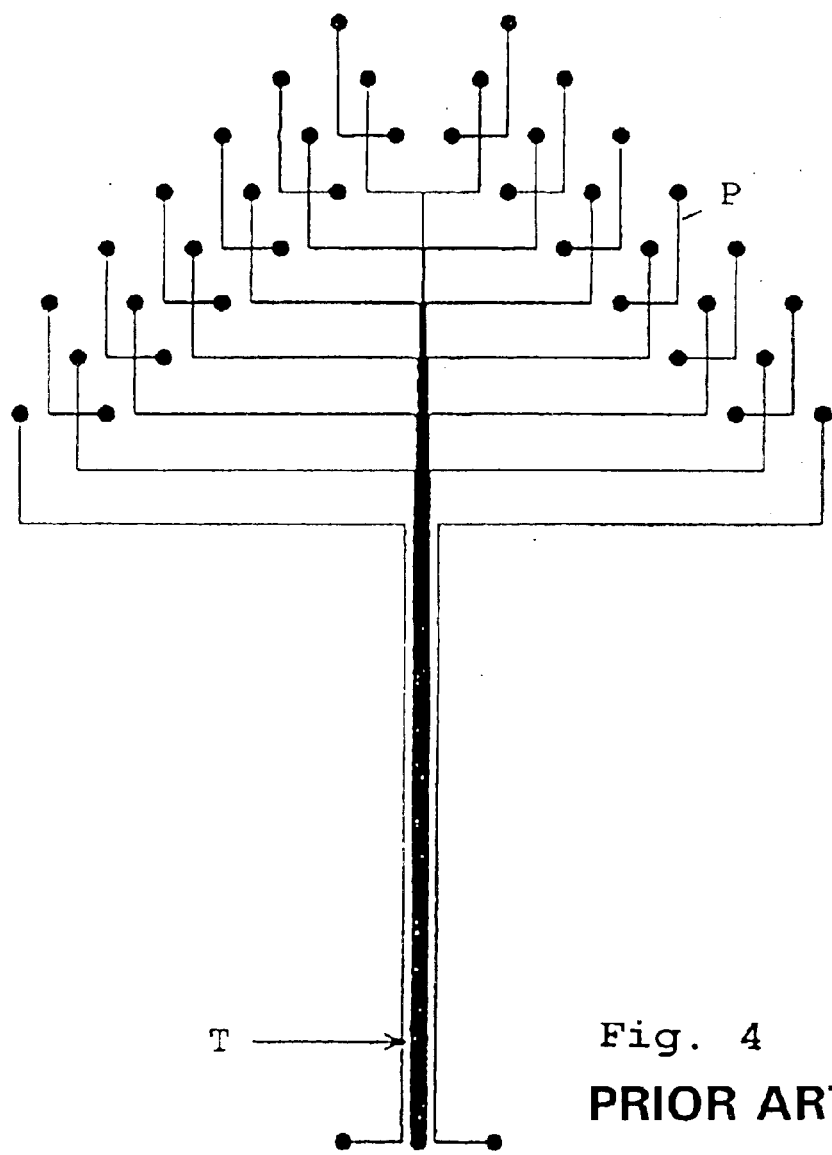

Additional advantages and characteristics of the invention are illustrated in the following description of the attached drawings. Shown on:

FIG. 1 is a diagrammatic top view of an electrophoresis device according to the invention in an electrophoresis chamber, FIG. 2 is a magnified top view of the crossing of an injection channel with two separation channels, FIG. 3 is a diagrammatic view of a conventional electrophoresis device (prior art), and on FIG. 4 is another view of a conventional electrophoresis device (prior art).

In the following, the invention shall be described drawing reference to a preferred embodiment, in which a carrier chip with the channel structure according to the invention is provided as a separate part in an electrophoresis chamber. However, the invention can also be implemented with a one-piece design, in which the carrier chip is a fixed component of the electrophoresis chamber.

On FIG. 1, the electrophoresis device according to the invention encompasses numerous separation channels S, which extend from a first buffer reservoir P1 with a first electrode E1 to a second buffer reservoir P2 with a second electrode E2. Electrodes E1, E2 subjected to a voltage (separation voltage) designed to generate an electrical field strength in the separation channels S, during exposure to which the samples migrate through the separation channels with substance-specific migration rates. The separation channels S run precisely in a carrier chip C between the respectively adjacent buffer reservoirs P1, P2.

The separation channels S are crossed by the injection channel I near one of their ends. The injection channel I is also processed on the surface of the carrier chip C, but runs diagonally or transverse to the separation channels. To simplify the actuation and standardize the separation paths, the injection channel is also straight, and essentially runs perpendicular to the orientation of the separation channels. Electrodes E3, E4 are provided at the ends of the injection channel I, i.e., on either side of the area intersected by the separation channels S. Electrodes E3, E4 are placed under a voltage to generate a field strength in the injection channel I, during exposure to which the sample injection takes place from an application area into one of the separation channels (injection voltage), respectively. The injection voltage is a d.c. voltage with a suitable polarity. After injection, the molecules can additionally be concentrated at special zones through exposure to an electrical field. A detection zone D is provided at the opposing end of the separation channels S. The substances separated in the separation channels based on their varying migration rates are detected in the detection zone D. Detection takes place in a known manner, e.g., via fluorescence measurements, or the like.

In the embodiment shown, the separation channels S are roughly 5 cm long. The separation channel width can range from several 100 $\mu$m to roughly 20 $\mu$m. However, these values can vary depending on the application. The separation voltage between the electrodes E1, E2 and injection voltage between the electrodes E3, E4 are selected as a function of the desired electrical parameters, size correlations and electrical properties of the separation medium, as known for conventional electrophoresis devices with a crossed structure. However, the injection voltage is multiply increased relative to the injection voltage at a single crossed structure according to FIG. 1 based on the number of separation channels S, so that a high enough partial injection voltage is formed at a crossing point between the injection channel I and a separation channel S taking into account the voltage drop at the remaining parts of the injection channel I.

The carrier chip has a cover (not shown) for the separation channels S, which leaves open the injection channel I or the application areas A (see below) thereof. The cover, e.g., a film (or liquid with a lower density), is used to prevent contamination and to generate reproducible characteristics of the separation paths along the separation channels S.

The carrier chip C can be inserted into the electrophoresis chamber A between the buffer reservoirs P1, P2. Mounts (not shown) can be provided on the electrophoresis chamber K to more accurately position the carrier chip C.

FIG. 2 shows a magnified section of the surface of carrier chip C with two separation channels S and the injection channel I. The diagrammatic view according to FIG. 2 shows the separation channels with a larger width than the injection channel. This relationship can be reversed depending on the application. In particular, the width of the injection channel can be selected as a function of application relative to a desired separation resolution. Since the area on which a separated substance is distributed (so-called band or peak) cannot be narrower than the injection channel after separation, a sufficiently narrow injection channel must be selected for highly resolving electrophoretic separations. Near each crossing point, the injection channel I has an application area A, which is provided for sample loading. In turn, the application area A can have a surface enlarged relative to the injection channel I, depending on the application. Such an expanded channel (e.g., funnel-shaped) has advantages with respect to the accuracy of sample loading with a micro-dispenser. The position of application area A relative to the adjacent separation channel S or the polarity of the injection voltage applied to the electrodes E3, E4 is selected in such a way that a sample positioned in the application area migrates into the adjacent separation channel S during exposure to an electrical field.

On the side of the crossing points opposite the application area A, FIG. 2 shows a sample barrier, e.g., in the form of a molecule trap M. The sample barrier can consist of a channel expansion, a semi-permeable membrane (e.g., dialysis membrane) that allows passage of buffer ions but retains sample molecules, or a three-dimensional, porous structure (e.g., a gel), which is also permeable to the buffer ions, but impermeable or an impediment to biological macromolecules. In the case of the channel expansion, the barrier effect is based on the local reduction in the density of the electrical field lines, which considerably slows the sample molecules in this area, so that sample molecules cannot reach the application area A of the next separation channel S for the duration of the separation time along the separation channels S.

A sample barrier or molecule trap M is not compulsory. As an alternative, the geometric and electrical properties of the electrophoresis device can be selected in such a way that the migration of samples in the injection channel does not take place beyond the respective crossing area during the injection phase.

The electrophoresis device according to the invention is used based on the steps described below.

A carrier chip C is prepared for the separation procedure by loading it with the separation medium and covering it. The cover can be a film that leaves open the injection channel at the application areas A. The prepared carrier chip C is placed into the electrophoresis chamber A. This placement process can be automated, e.g., with a positioning device (robot). The insertion of carrier chip C is comparable to the placement of a two-dimensional separation gel in a corresponding electrophoresis device during gel electrophoresis. The electrophoresis chamber is then filled with buffer solution. Filling takes place in such a way that the buffer reservoir P1, P2 is filled with the buffer solution, so that the ends of the separation channels S are covered. As a result, there is a connection between the buffer solution in the buffer reservoirs P1, P2 and the separation medium in the channels. Filling takes place in such a way that the surface of the carrier chip C with the cover film (not shown) is not covered. To this end, suitable barriers can be provided on the long sides of the carrier chip C down to the buffer reservoirs. The application areas are then loaded with a micro-dispenser.

The micro-dispenser encompasses one or more elements (capillaries, metal pins, micro-pipettes, micro-drop injectors, e.g., with piezoelectric trigger). Preferably, a micro-dispenser with programmable increments in the $\mu$m range is used to permit a defined sample loading in the application areas A. The application areas A can be loaded simultaneously with a series of micro-dispensers (corresponding to the number of separation channels S), or serially with individual micro-dispensers.

After the application areas have been loaded with the samples to be analyzed (sample mixtures), the latter migrate between the electrodes E3, E4 to the adjacent separation channel S during exposure to the electrical field, and fill the respective crossing area. After this injection phase, the field between the electrodes E3, E4 is deactivated. The analyzed material can now be additionally concentrated in electrically chargeable zones situated at the beginning of the separation channel. An electrical field is then formed between the electrodes E1, E2. Under influence of this field, the analyzed material is transported in the direction of detection zone D, and separated by the movement in the separation matrix (gel, polymer solution). Depending on the physicochemical properties of the components or constituents in the sample mixtures, the latter reach the detection zone D in a time-displaced manner, where they can be individually identified. A predetermined, small electrical field can be formed between the electrodes E3, E4 during the separation phase to maintain a homogeneous field in the separation channel S.

Therefore, the separation process can consist of three phases:

Phase 1: Loading all or numerous application areas with a micro-dispenser device, preferably simultaneously or narrowly spaced apart, Phase 2: Electrical injection through simultaneous filling of all crossing points between the injection channel and separation channels during exposure to an electrical field, with subsequent possible concentration at zones specially provided for this purpose, and Phase 3: Parallel separation of all samples in the separation channels.

After the detection of constituents making up the analyzed material in the detection zone D (end of electrophoretic separation), the carrier chip C can be removed from the electrophoresis chamber A and disposed. The electrophoresis chamber K is available for the ensuing separation with a new carrier chip C.

The described progression can be fully automated. Suitable positioning devices place the carrier chip in the electrophoresis chamber, and position the micro-dispenser(s) at the application areas A. The positioning device can be equipped with an image recorder to simplify positioning of the micro-dispenser relative to the carrier chip C.

What is claimed is:

1. An electrophoresis device with a plurality of separation channels that can be separately loaded with samples, which are each connected with a sample channel, from which samples can be injected into the respective separation channel during exposure to an electrical field, wherein the sample channels are interconnected, thereby forming a shared injection channel that intersects the separation channels at crossing points, and whose ends have electrodes for generating the electrical field exposure, wherein the injection channel has plural exposed application areas, one area adjacent to each separation channel on a predetermined side of the respective crossing point, each said application area being designed and configured for taking samples by means of a micro-dispenser, wherein said injection channel further comprises a sample barrier on the side disposed opposite the application area for each crossing point where the injection channel and the separation channel are linked.

2. The electrophoresis device according to claim 1, in which the injection channel has channel expansions at said application areas.

3. The electrophoresis device according to claim 1, in which the sample barrier for each separation channel further comprises a molecule trap on the side of the respective crossing point lying opposite the respective application area.

4. The electrophoresis device according to claim 3, in which the molecule trap is a channel expansion, a semi-permeable membrane or a three-dimensional, porous structure.

5. The electrophoresis device according to claim 1, in which the separation channels and the injection channel are incorporated on a carrier chip, which is part of an electrophoresis chamber with buffer reservoirs each with one electrode.

6. The electrophoresis device according to claim 5, in which the carrier chip is designed for disposable use and can be detached from the electrophoresis chamber.

7. The electrophoresis device according to claim 1 wherein said electrophoresis device is shaped and configured to be used with an analyzer, and which has at least one micro-dispenser to supply the sample on the application areas of the injection channels.

8. A method for performing electrophoresis comprising providing the electrophoresis device according to claim 1, wherein the sample channels are loaded with samples by means of a micro-dispenser, and the samples are introduced into the injection channel near the crossing point between the injection channel and one respective separation channel for purposes of sample separation, and transferred into the separation channel by exposing the injection channel to an electrical field, with electrophoretic separation taking place in this separation channel.

9. The method according to claim 8, in which the samples are electrically concentrated prior to separation at predetermined zones at the beginning of the separation channel.

* * * * *